United States Patent [19]
Kirwan, Jr.

[11] Patent Number: 5,957,928
[45] Date of Patent: Sep. 28, 1999

[54] HANDPIECE FOR IRRIGATION AND ASPIRATION DURING EYE SURGERY AND A METHOD FOR MANUFACTURING SUCH A HANDPIECE

[75] Inventor: Lawrence T. Kirwan, Jr., Pembroke, Mass.

[73] Assignee: Kirwan Surgical Products, Inc., Marshfield, Mass.

[21] Appl. No.: 09/094,175

[22] Filed: Jun. 9, 1998

[51] Int. Cl.⁶ .............................. A61F 9/007; A61M 5/00
[52] U.S. Cl. .............................................. 606/107; 604/43
[58] Field of Search .............................. 606/107; 604/27, 604/19, 35, 43

[56] References Cited

U.S. PATENT DOCUMENTS

| | | | |
|---|---|---|---|
| 3,929,126 | 12/1975 | Corsaut | 604/43 |
| 4,014,333 | 3/1977 | McIntyre | 604/43 |
| 4,320,761 | 3/1982 | Haddad | 606/7 |
| 4,553,957 | 11/1985 | Williams et al. | 604/43 |
| 4,682,978 | 7/1987 | Martin | 604/43 |
| 4,705,500 | 11/1987 | Reimels et al. | 604/35 |
| 4,825,865 | 5/1989 | Zelman | 606/6 |
| 4,869,716 | 9/1989 | Smirmaul | 604/22 |
| 4,891,044 | 1/1990 | Mitchell | 604/27 |
| 4,904,238 | 2/1990 | Williams | 604/43 |
| 4,993,432 | 2/1991 | Shields et al. | 128/838 |
| 5,057,098 | 10/1991 | Zelman | 606/6 |
| 5,084,012 | 1/1992 | Kelman | 604/35 |
| 5,139,504 | 8/1992 | Zelman | 606/127 |
| 5,151,083 | 9/1992 | Pichler | 604/22 |
| 5,195,959 | 3/1993 | Smith | 604/34 |
| 5,213,569 | 5/1993 | Davis | 604/22 |
| 5,242,387 | 9/1993 | Loughlin | 604/43 |
| 5,322,504 | 6/1994 | Doherty et al. | 606/167 |
| 5,558,634 | 9/1996 | Mitchell | 604/35 |
| 5,562,612 | 10/1996 | Fox | 604/27 |
| 5,609,573 | 3/1997 | Sandock | 604/22 |
| 5,743,871 | 4/1998 | Sturkel et al. | 604/35 |
| 5,746,713 | 5/1998 | Hood et al. | 604/22 |
| 5,807,310 | 9/1998 | Hood | 604/22 |
| 5,873,851 | 2/1999 | Nilsson | 604/43 |
| 5,879,356 | 3/1999 | Geuder | 606/107 |

*Primary Examiner*—Paul J. Hirsch
*Assistant Examiner*—Michael B. Priddy
*Attorney, Agent, or Firm*—Weingarten, Schurgin, Gagnebin & Hayes LLP

[57] ABSTRACT

A method for manufacturing an irrigation/aspiration (I/A) handpiece for use during cataract eye surgery and the I/A handpiece so manufactured are provided. The I/A handpiece comprises an aspiration cannula which extends through a hollow, inseparable housing assembly to an aspiration port, and an irrigation cannula concentrically surrounding a portion of the aspiration cannula outside the housing assembly. The irrigation cannula is in fluid communication with a hollow interior region of the housing assembly, including an irrigation port. The I/A handpiece is manufactured by insert molding the irrigation cannula within a front housing. The aspiration cannula is inserted through the irrigation cannula and the front housing and within a rear housing which contains the aspiration and irrigation ports. An interconnecting member is molded to fill the gap between the front housing and the rear housing, thereby providing an integral, inseparable housing assembly. The I/A handpiece is readily cleanable without requiring disassembly.

14 Claims, 2 Drawing Sheets

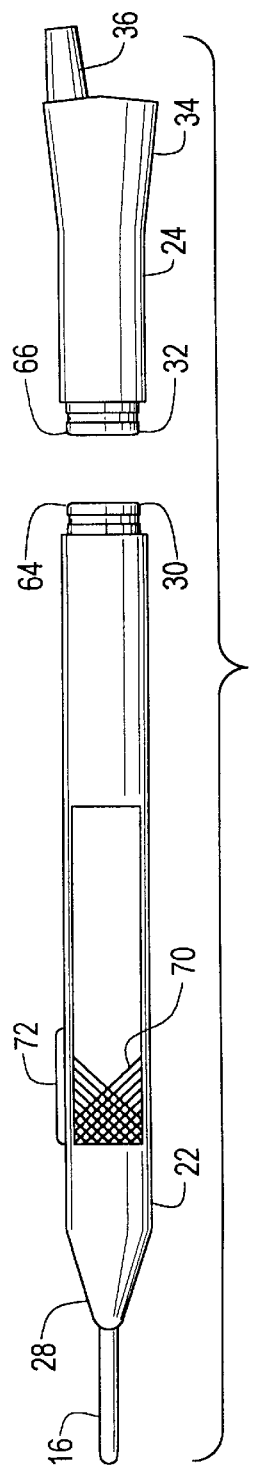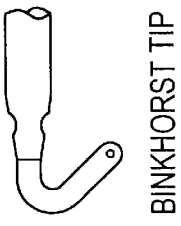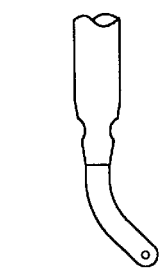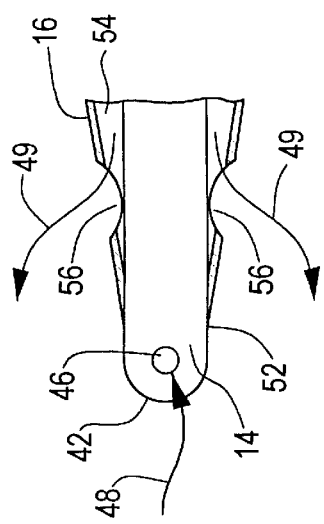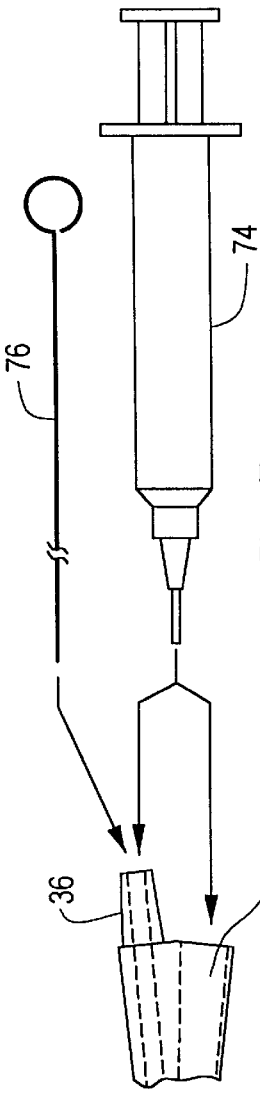

5,957,928

HANDPIECE FOR IRRIGATION AND ASPIRATION DURING EYE SURGERY AND A METHOD FOR MANUFACTURING SUCH A HANDPIECE

CROSS REFERENCE TO RELATED APPLICATIONS

None

STATEMENT REGARDING FEDERALLY SPONSORED RESEARCH OR DEVELOPMENT

Not Applicable

BACKGROUND OF THE INVENTION

In cataract surgery on the eye, after the lens is removed, a jagged edge of cortical material or cortex is left in the eye. This cortical material is removed by an instrument known as an irrigation and aspiration (I/A) handpiece. The I/A handpiece consists of two cannulas or tubes. The cortical material is aspirated under vacuum through one cannula to remove it. Simultaneously, an irrigating fluid, such as a saline solution, flows through the other cannula to prevent the material in the eye from drying and collapsing and to assist in the removal of the cortical material. The cannulas may be adjacent or concentric. When concentric, the inner cannula generally comprises the aspiration cannula and the outer cannula the irrigation cannula.

Commercially available I/A handpieces having concentric cannulas fall generally into two types. A first type is reusable after sterilization in an autoclave. This type must be disassembled to be cleaned and is fairly expensive to manufacture. A second type is disposable and cheaper to manufacture.

BRIEF SUMMARY OF THE INVENTION

The present invention relates to an irrigation and aspiration (I/A) handpiece which is sterilizable and reusable, but which does not have to be disassembled for cleaning.

The I/A handpiece comprises an integral or unitary, inseparable housing assembly for supporting concentric irrigation and aspiration tubes or cannulas. The housing assembly comprises a hollow, generally tubular body having an interior region and extending from a nose to a tail section. The generally tubular body is formed from a front housing, which includes the nose, and a rear housing, which includes the tail section. The front housing and rear housing are inseparably connected by an interconnecting member. An aspiration port and an irrigation port are formed within the tail section. The irrigation port is in fluid communication with the interior region of the housing assembly. The aspiration port is connectable to a vacuum source and the irrigation port is connectable to a source of irrigation fluid.

The irrigation cannula comprises a hollow, generally tubular body which extends from a fluid entrance to a tip end. At least one irrigation opening is located adjacent the tip end. The fluid entrance is fixed within the nose of the housing assembly to be in fluid communication with the interior region. In this manner, irrigation fluid is flowable through the irrigation port, the interior region, the irrigation cannula and out the irrigation opening.

The aspiration cannula comprises a hollow, generally tubular body which extends from a tip to a fluid exit. An aspiration opening is located adjacent the tip. The tubular body extends concentrically through the irrigation cannula and the interior region of the housing assembly, and the fluid exit is located within the aspiration port of the housing assembly. The aspiration opening protrudes from the tip end of the irrigation cannula. In this manner, aspirated matter is flowable through the aspiration opening, the tubular body of the aspiration cannula, and the aspiration port.

The I/A handpiece is manufactured by forming the front housing with the fluid entrance of the irrigation cannula fixed within the nose of the housing assembly, as by insert molding. The rear housing is molded separately. The aspiration cannula is then supported in the interior region of the housing assembly with its fluid exit within the aspiration port and the aspiration opening protruding beyond the tip end of the irrigation cannula. The front housing and the rear housing are supported with a gap separating them. The interconnecting member is formed within the gap between the front housing and the rear housing, as by molding. In this manner, the housing assembly becomes an integral, inseparable assembly.

BRIEF DESCRIPTION OF THE SEVERAL VIEWS OF THE DRAWING

The invention will be more fully understood from the following detailed description taken in conjunction with the accompanying drawings in which:

FIG. 3 is a side view of the front and rear housings of the irrigation/aspiration handpiece during manufacture;

FIG. 4 is a partial view of the tips of the irrigation and aspiration cannulas;

FIG. 5 is an illustration of a cleaning procedure for the irrigation/aspiration handpiece according to the present invention;

FIG. 6 is a partial view of a curved tip for an irrigation/aspiration handpiece; and FIG. 7 is a partial view of a Binkhorst tip for an irrigation/aspiration handpiece.

DETAILED DESCRIPTION OF THE INVENTION

Figure 1:
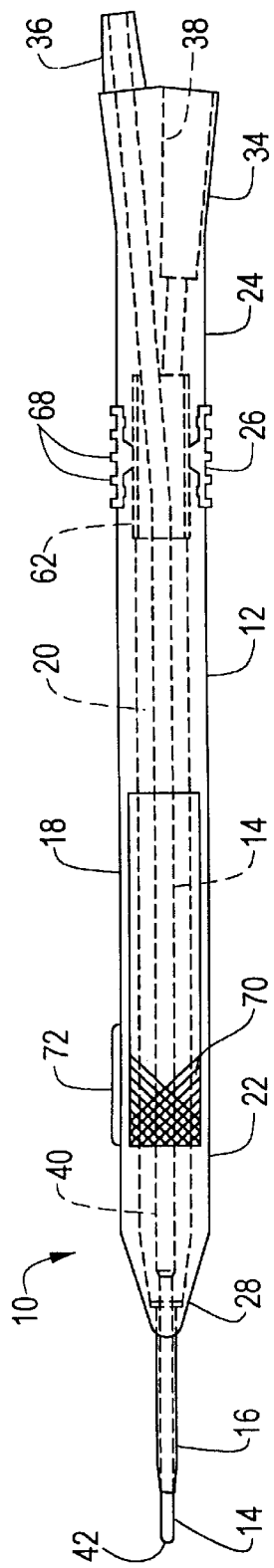
FIG. 1 is a side view of an irrigation/aspiration handpiece according to the present invention.
Figure 2:
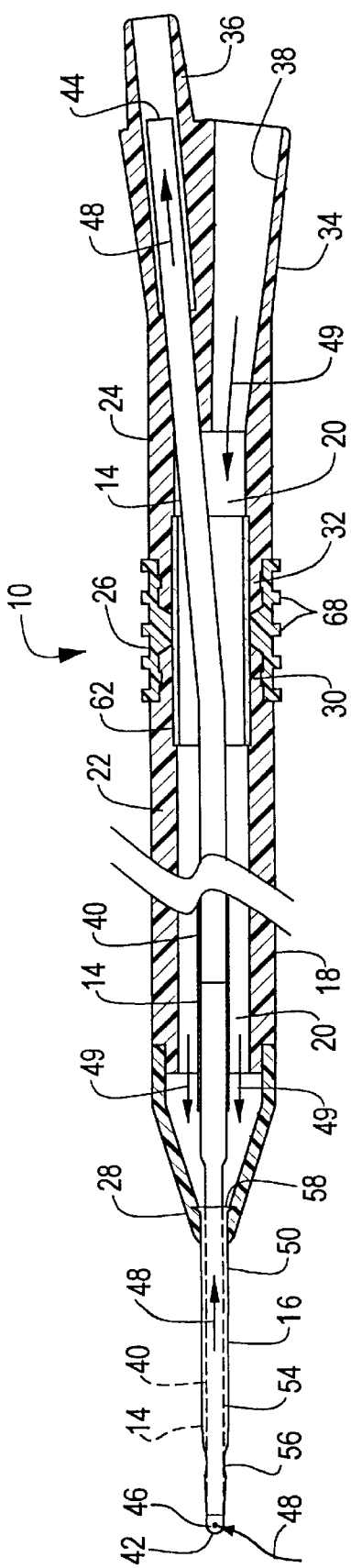
FIG. 2 is a cross-sectional view of the irrigation/aspiration handpiece of FIG. 1.

Referring to FIGS. 1 through 3, an irrigation/aspiration (I/A) handpiece 10 includes a housing assembly 12 supporting an aspiration cannula 14 and an irrigation cannula 16 concentrically disposed around the aspiration cannula.

The housing assembly is a generally tubular, hollow body 18 having an interior region 20 which also serves as a channel for the irrigation fluid. The housing assembly is preferably formed by a front housing 22, a rear housing 24, and an interconnecting member 26. The front housing extends from a nose 28, which may be tapered, to a narrowed end piece 30. The rear housing 24 extends from a narrowed front piece 32 to a tail section 34. The hollow interior region 20 of the housing assembly diverges within the tail section to an aspiration port 36 connectable to a vacuum line (not shown) for aspiration and an irrigation port 38 connectable to a source of irrigation fluid (not shown). The irrigation port may be a luer or tapered channel. The tail section 34 may be widened to accommodate the aspiration and irrigation ports, as necessary. The housing assembly is formed of any suitable moldable plastic material, such as a sterilizable polypropylene or other thermoplastic. Preferably, the material is chosen to withstand sterilizable temperatures.

The aspiration cannula 14 comprises a hollow, generally tubular body 40 which extends from a tip 42 to a fluid exit 44. The tip 42 is located outside the housing assembly 12, and a small opening 46 is located adjacent the tip. The cannula extends through the interior region within the housing assembly, terminating at the fluid exit 44 within the aspiration port 36. The cannula may be angled slightly to conform to the orientation of the aspiration port, if the aspiration port is, for example, angled. When a vacuum line is connected to the aspiration port, material may be drawn through the opening in the tip end, down the cannula, and out the aspiration port, indicated by arrows 48. The aspiration cannula is preferably formed of a metal, such as a 300 series stainless steel.

The irrigation cannula 16 comprises a hollow, generally tubular body 50 which concentrically surrounds a portion of the aspiration cannula. The irrigation cannula includes a tip end 52 outside the housing assembly which is recessed slightly from the tip 42 of the aspiration cannula so that the aspiration opening 46 is not blocked. The irrigation cannula is spaced from the aspiration cannula to provide an annular channel 54 through which irrigation fluid may flow and includes one or more openings 56 adjacent the tip end 52 through which the irrigation fluid may flow outwardly. Typically, two openings are provided, oriented 180° to each other. A fluid entrance 58, opposite the tip end, is fixed inside the nose 28 of the front housing 22 for fluid communication with the channel defined by the hollow interior region 20 of the housing assembly. When a source of irrigation fluid is connected to the irrigation port 38, irrigation fluid may flow through the irrigation port into the interior region 20, the fluid entrance 58, the channel 54 in irrigation cannula 16, and out the irrigation openings 56, indicated by arrows 49. The irrigation cannula is preferably formed of a metal, such as a 300 series stainless steel.

To manufacture the I/A handpiece, the cannulas 14, 16 are formed by any suitable process, such as a deep drawing or eyeletting process from flat, circular discs. The openings 46, 56 are formed in the cannulas, and the tip end of the irrigation cannula may be swaged downed down to provide a close tolerance fit around the aspiration cannula.

The irrigation cannula 16 is supported in a mold to be insert molded into the nose 28 of the front housing 22. The front housing may be formed as a single piece, or the tapered nose 22 of the housing may be formed separately from the remainder of the front housing if desired. The rear housing 24 is molded separately from the front housing. The aspiration cannula 14 is inserted through the irrigation cannula until the fluid exit 44 protrudes out the end piece 30 of the front housing while the opening 46 at the tip 42 still protrudes from the irrigation cannula 16. The aspiration opening 46 is oriented 90° from the irrigation openings 56. The fluid exit of the aspiration cannula is placed within the aspiration port of the rear housing.

The front and rear housings 22, 24 are then supported in a mold closely adjacent to each other with the cannulas therein. A small gap remains between the two housings. If desired, a sleeve 62 may be placed over the aspiration cannula at the location of the gap to better support the front and rear housings. The interconnecting member 26 is then injection molded to form a band within the gap between the housings and around the narrowed end piece 30 and front piece 32, to fill the gap and join the two housings together. The narrowed pieces preferably include an annular recess 64, 66 to better anchor the interconnecting member thereto. In this manner, the front and rear housings and the interconnecting member form an integral or unitary, inseparable housing assembly.

The interconnecting member may include ribs 68 or other textures for improved gripping by a surgeon's hand, particularly during connection of the vacuum source and irrigation fluid source to the aspiration port and irrigation port respectively. Similarly, portions of the front housing may include a texture 70 for improved gripping by the surgeon during the surgical procedure. An orientation feature 72 may be included on the housing assembly. The aspiration opening in the tip end of the aspiration cannula is preferably aligned 1800 from this feature. This feature informs the surgeon where the aspiration opening is located, since the opening is extremely small and difficult to see with the unaided eye.

Referring to FIG. 5, to clean the I/A handpiece, a cleaning solution is injected, for example, with a syringe 74, in both the irrigation port 38 and the aspiration port 36. From the irrigation port, the cleaning solution passes through the hollow region of the housing assembly, through the irrigation cannula, and out the irrigation openings. From the aspiration port, the cleaning solution passes through the aspiration cannula and out the aspiration opening adjacent the tip of the aspiration cannula. If the aspiration cannula becomes blocked, a stylet 76 can be inserted through the aspiration port and the aspiration cannula to push out the blockage.

The aspiration cannula can include a number of different tip configurations, as are known in the art, such as a curved tip (FIG. 6) or a Binkhorst tip (FIG. 7). It will be appreciated, however, that if a curved or Binkhorst tip is used, the stylet may be unable to remove any blockages in the aspiration cannula.

The invention is not to be limited by what has been particularly shown and described, except as indicated by the appended claims.

I claim:

1. A method for manufacturing an irrigation and aspiration handpiece for use in eye surgery, comprising:

providing an aspiration cannula comprising a hollow, generally tubular body extending from a tip to a fluid exit, an aspiration opening located adjacent the tip;

providing an irrigation cannula comprising a hollow, generally tubular body extending from a tip end to a fluid entrance, at least one irrigation opening located adjacent the tip end, the irrigation cannula having an inner diameter greater than an outer diameter of the aspiration cannula;

forming an integral inseparable housing assembly comprising a hollow, generally tubular body having an interior region extending from a nose to a tail section and including an aspiration port and an irrigation port in the tail section, with the irrigation cannula fixed at the fluid entrance to the nose of the housing assembly, and with the aspiration cannula supported in the interior region of the housing assembly with the fluid exit within the aspiration port and the aspiration opening protruding beyond the tip end of the irrigation cannula.

2. The method of claim 1, wherein the housing assembly is formed by molding.

3. The method of claim 1, wherein the forming step further comprises:

forming a hollow front housing supporting the irrigation cannula, and forming a hollow rear housing including the aspiration port and the irrigation port;

supporting the front housing and the rear housing separated by a gap, with the irrigation cannula fixed to the front housing, and with the aspiration cannula extending concentrically through the irrigation cannula and through the front housing and with the fluid exit located within the aspiration port of the rear housing; and forming an interconnecting member within the gap between the front housing and the rear housing.

4. The method of claim 3, wherein the front housing is formed by molding with the irrigation cannula supported within the mold.

5. The method of claim 3, wherein the interconnecting member is formed by molding.

6. The method of claim 1, further comprising supporting the aspiration cannula within the housing assembly with a sleeve during the forming step.

7. The method of claim 1, wherein the aspiration cannula and the irrigation cannula are formed of a metal.

8. The method of claim 1, wherein the front housing, the rear housing, and the interconnecting member are formed of a plastic material.

9. An irrigation and aspiration handpiece for eye surgery, comprising:

an integral, inseparable housing assembly comprising a hollow, generally tubular body having an interior region and extending from a nose to a tail section, an aspiration port and an irrigation port formed within the tail section, the irrigation port in fluid communication with the interior region;

an irrigation cannula comprising a hollow, generally tubular body extending from a tip end to a fluid entrance, at least one irrigation opening located adjacent the tip end, the fluid entrance fixed within the nose of the housing assembly to be in fluid communication with the interior region, whereby irrigation fluid is flowable through the irrigation port, the interior region, the irrigation cannula and out the irrigation opening;

an aspiration cannula comprising a hollow, generally tubular body extending from a tip to a fluid exit, an aspiration opening located adjacent the tip, the tubular body extending through the irrigation cannula and the interior region of the housing assembly, and the fluid exit located within the aspiration port of the housing assembly, the aspiration opening protruding from the tip end of the irrigation cannula, whereby aspirated matter is flowable through the aspiration opening, the tubular body of the aspiration cannula, and the aspiration port.

10. The handpiece of claim 9, wherein the housing assembly is formed of a plastic material.

11. The handpiece of claim 9, wherein the aspiration cannula and the irrigation cannula are formed of a metal material.

12. The handpiece of claim 9, wherein:

the housing assembly is formed of a front housing, a rear housing, and an interconnecting member between the front housing and the rear housing; and the front housing, the rear housing, and the interconnecting member are integrally and inseparably connected.

13. The handpiece of claim 9, wherein the housing assembly includes a textured outer surface for gripping.

14. The handpiece of claim 9, wherein the housing assembly includes an orientation feature located to provide a visual indication of the position of the aspiration opening.

* * * * *

UNITED STATES PATENT AND TRADEMARK OFFICE
CERTIFICATE OF CORRECTION

PATENT NO : 5,957,928
DATED : September 28, 1999
INVENTOR(S) : Lawrence T. Kirwan, Jr.

It is certified that error appears in the above-identified patent and that said Letters Patent are hereby corrected as shown below:

```
Column 4, line 10, "1800", should read --180°--; and

Column 5, line 15, "claim 1", should read --claim 3--.
```

Signed and Sealed this

First Day of May, 2001

Attest:

NICHOLAS P. GODICI

*Attesting Officer*    *Acting Director of the United States Patent and Trademark Office*